US00PP24350P2

(12) United States Plant Patent
Isobe

(10) Patent No.: US PP24,350 P2
(45) Date of Patent: Mar. 25, 2014

(54) *PETUNIA* PLANT NAMED 'SUNSURF DEPAUSA'

(50) Latin Name: *Petunia×hybrida*
Varietal Denomination: Sunsurf Depausa

(75) Inventor: Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 122 days.

(21) Appl. No.: 13/506,171

(22) Filed: Mar. 31, 2012

(51) Int. Cl.
*A01H 5/00* (2006.01)

(52) U.S. Cl.
USPC ..... Plt./356.21

(58) Field of Classification Search
USPC ..... Plt./356.21
See application file for complete search history.

(56) References Cited

U.S. PATENT DOCUMENTS

PP16,358 P3 * 3/2006 Iwaki et al. ..... Plt./356.22
PP19,294 P2 * 10/2008 Dummen ..... Plt./356.21

OTHER PUBLICATIONS

UPOV PLUTO 201303 CA Citation for 'Sunsurf Depausa' Apr. 30, 2012.*
UPOV PLUTO 201303 QZ Citation for 'Sunsurf Depausa' Jun. 15, 2012.*
Anonymous. Suntory Collection Europe. Spring 2013.*
Plant Varieties Journal Canada Apr. 15, 2012.*

* cited by examiner

*Primary Examiner* — Wendy C Haas
(74) *Attorney, Agent, or Firm* — C. A. Whealy

(57) ABSTRACT

A new and distinct cultivar of *Petunia* plant named 'Sunsurf Depausa', characterized by its compact, mounding and trailing plant habit; vigorous growth habit; freely branching habit; early and freely flowering habit; long flowering period; medium-sized dark red purple-colored flowers; and good garden performance.

1 Drawing Sheet

Botanical designation: *Petunia×hybrida*.
Cultivar denomination: 'SUNSURF DEPAUSA'.

BACKGROUND OF THE INVENTION

The present invention relates to a new and distinct cultivar of *Petunia* plant, botanically known as *Petunia×hybrida* and hereinafter referred to by the name 'Sunsurf Depausa'.

The new *Petunia* plant is a product of a planned breeding program conducted by the Inventor in Higashiomi, Shiga, Japan. The objective of the breeding program is to create new compact freely branching and freely flowering *Petunia* plants with mounding habit and attractive flower coloration.

The new *Petunia* plant originated from a cross-pollination made by the Inventor in March, 2008 in Higashiomi, Shiga, Japan of a proprietary selection of *Petunia×hybrida* identified as code name BW1, not patented, as the female, or seed, parent with a proprietary selection of *Petunia×hybrida* identified as code name PF411-5, not patented, as the male, or pollen, parent. The new *Petunia* plant was discovered and selected by the Inventor as a single flowering plant within the progeny of the stated cross-pollination in a controlled environment in Higashiomi, Shiga, Japan in October, 2008.

Asexual reproduction of the new *Petunia* plant by terminal cuttings in a controlled environment in Higashiomi, Shiga, Japan since October, 2008 has shown that the unique features of this new *Petunia* plant are stable and reproduced true to type in successive generations.

SUMMARY OF THE INVENTION

Plants of the new *Petunia* have not been observed under all possible environmental conditions and cultural conditions.

The phenotype may vary somewhat with variations in environmental conditions such as temperature and light intensity without, however, any variance in genotype.

The following traits have been repeatedly observed and are determined to be the unique characteristics of 'Sunsurf Depausa'. These characteristics in combination distinguish 'Sunsurf Depausa' as a new and distinct *Petunia* plant:

1. Compact, mounding and trailing plant habit.
2. Vigorous growth habit.
3. Freely branching habit.
4. Early and freely flowering habit.
5. Long flowering period.
6. Medium-sized dark red purple-colored flowers.
7. Good garden performance.

Plants of the new *Petunia* can be compared to plants of the female parent selection. Plants of the new *Petunia* differ primarily from plants of the female parent selection in plant habit as plants of the new *Petunia* are more trailing than and are not as upright as plants of the female parent selection. In addition, plants of the new *Petunia* have larger flowers than plants of the female parent selection.

Plants of the new *Petunia* can be compared to plants of the male parent selection. Plants of the new *Petunia* differ primarily from plants of the male parent selection in flower color as plants of the male parent selection have red-colored flowers. In addition, plants of the new *Petunia* have smaller flowers than plants of the male parent selection.

Plants of the new *Petunia* can also be compared to plants of the *Petunia* 'Sunpurple', disclosed in U.S. Plant Pat. No. 16,358. In side-by-side comparisons conducted in Higashiomi, Shiga, Japan, plants of the new *Petunia* and 'Sunpurple' differed primarily in the following characteristics:

1. Plants of the new *Petunia* were larger than plants of 'Sunpurple'.
2. Plants of the new *Petunia* had smaller leaves than plants of 'Sunpurple'.
3. Plants of the new *Petunia* had smaller flowers than plants of 'Sunpurple'.
4. Plants of the new *Petunia* and 'Sunpurple' differed in flower color as plants of 'Sunpurple' had lighter red purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Depausa' grown in a container.

The photograph at the bottom of the sheet is a close-up view of a typical flowering plant of 'Sunsurf Depausa'.

DETAILED BOTANICAL DESCRIPTION

The aforementioned photographs and following observations, measurements and values describe plants grown during the spring in 15-cm containers in an outdoor nursery in Higashiomi, Shiga, Japan and under cultural practices typical of commercial production. During the production of the plants, day temperatures averaged 23° C. and night temperatures averaged 13° C. Plants were four months old when the photographs and description were taken. In the following description, color references are made to The Royal Horticultural Society Colour Chart, 2001 Edition, except where general terms of ordinary dictionary significance are used.

Botanical classification: *Petunia×hybrida* 'Sunsurf Depausa'.

Parentage:

*Female, or seed, parent*.—Proprietary selection of *Petunia×hybrida* identified as code name BW1, not patented.

*Male, or pollen, parent*.—Proprietary selection of *Petunia×hybrida* identified as code name PF411-5, not patented.

Propagation:

*Type*.—By terminal cuttings.

*Time to initiate roots*.—About one week at temperatures of 15° C. to 20° C.

*Time to produce a rooted young plant*.—About three weeks at temperatures of 15° C. to 20° C.

*Root description*.—Fibrous; white in color.

*Rooting habit*.—Freely branching.

Plant description:

*Plant and growth habit*.—Compact, mounding and trailing plant habit; freely branching habit with numerous lateral branches developing per plant; pinching enhances lateral branch development; vigorous growth habit.

*Plant height*.—About 16.9 cm.

*Plant diameter*.—About 53.4 cm.

Lateral branch description:

*Length*.—About 21.2 cm.

*Diameter*.—About 1.6 mm.

*Internode length*.—About 2.3 cm.

*Strength*.—Strong, flexible.

*Aspect*.—Upright to outwardly.

*Texture*.—Pubescent.

*Color*.—Close to N144C tinted with close to 74A.

Foliage description:

*Arrangement*.—Alternate, simple.

*Length*.—About 2.8 cm.

*Width*.—About 1.4 cm.

*Shape*.—Elliptic.

*Apex*.—Acute.

*Base*.—Obtuse.

*Margin*.—Entire.

*Texture, upper and lower surfaces*.—Sparsely pubescent.

*Venation pattern*.—Pinnate; reticulate.

*Color*.—Developing and fully expanded leaves, upper surface: Close to 137B; venation, close to 143B. Developing and fully expanded leaves, lower surface: Close to 137D; venation, close to 143C.

*Petioles*.—Length: About 6 mm. Diameter: About 1.5 mm. Texture, upper and lower surfaces: Pubescent. Color, upper and lower surfaces: Close to 143B.

Flower description:

*Flower arrangement and habit*.—Single salverform flowers arising from upper leaf axils; freely flowering habit with usually about 79 flowers developing per plant; flowers face upright to outwardly.

*Fragrance*.—None detected.

*Natural flowering season*.—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 4.9 cm.

*Flower length (depth)*.—About 4.7 cm.

*Throat diameter*.—About 1.1 cm.

*Tube diameter, base*.—About 4.3 mm.

*Tube length*.—About 2.5 cm.

*Flower buds*.—Shape: Cylindrical. Length: About 3.7 cm. Diameter: About 6.8 mm. Color: Close to 79B.

*Corolla*.—Arrangement: Five petals fused at the base and opening into a flared trumpet. Petal length from throat: About 4.7 cm. Petal width: About 2.3 cm. Petal shape: Spatulate. Petal apex: Mucronate. Petal margin: Entire, undulate. Petal texture, upper and lower surfaces: Smooth, glabrous. Throat texture: Smooth, glabrous. Tube texture: Pubescent. Color: Petal, when opening, upper surface: Close to 72A; venation, close to N79A. Petal, when opening, lower surface: Close to N74A; venation, close to N79A. Petal, fully opened, upper surface: Close to 72A; venation, close to N79A. Petal, fully opened, lower surface: Close to N80A; venation, close to N79A. Throat: Close to N79A. Tube: Close to 79A.

*Calyx*.—Arrangement: One star-shaped calyx tube with five sepals fused at the base per flower. Sepal length: About 1.6 cm. Sepal width: About 3.2 mm. Sepal shape: Narrowly elliptic. Sepal apex: Obtuse. Sepal margin: Entire. Sepal texture, upper and lower surfaces: Pubescent. Color: Developing sepals, upper surface: Close to 143A. Developing sepals, lower surface: Close to 143C. Fully developed sepals, upper surface: Close to 71A. Fully developed sepals, lower surface: Close to 143C.

*Peduncles*.—Length: About 2.4 cm. Diameter: About 1.1 mm. Strength: Strong. Texture: Pubescent. Color: Close to N144C; towards the apex, tinted with close to 71A.

*Reproductive organs*.—Stamens: Quantity per flower: Five. Stamen length: About 1.5 cm to 2.1 cm. Anther shape: Ellipsoidal. Anther size: About 2.8 mm by 1.9 mm. Anther color: Close to N82A. Pollen amount: Abundant. Pollen color: Close to N89C. Pistils: Quantity per flower: One. Pistil length: About 1.9 cm. Style color: Close to 83A and 154D. Stigma shape: Transversely ellipsoidal. Stigma color: Close to 83A. Ovary color: Close to N144C. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Depausa' as illustrated and described.

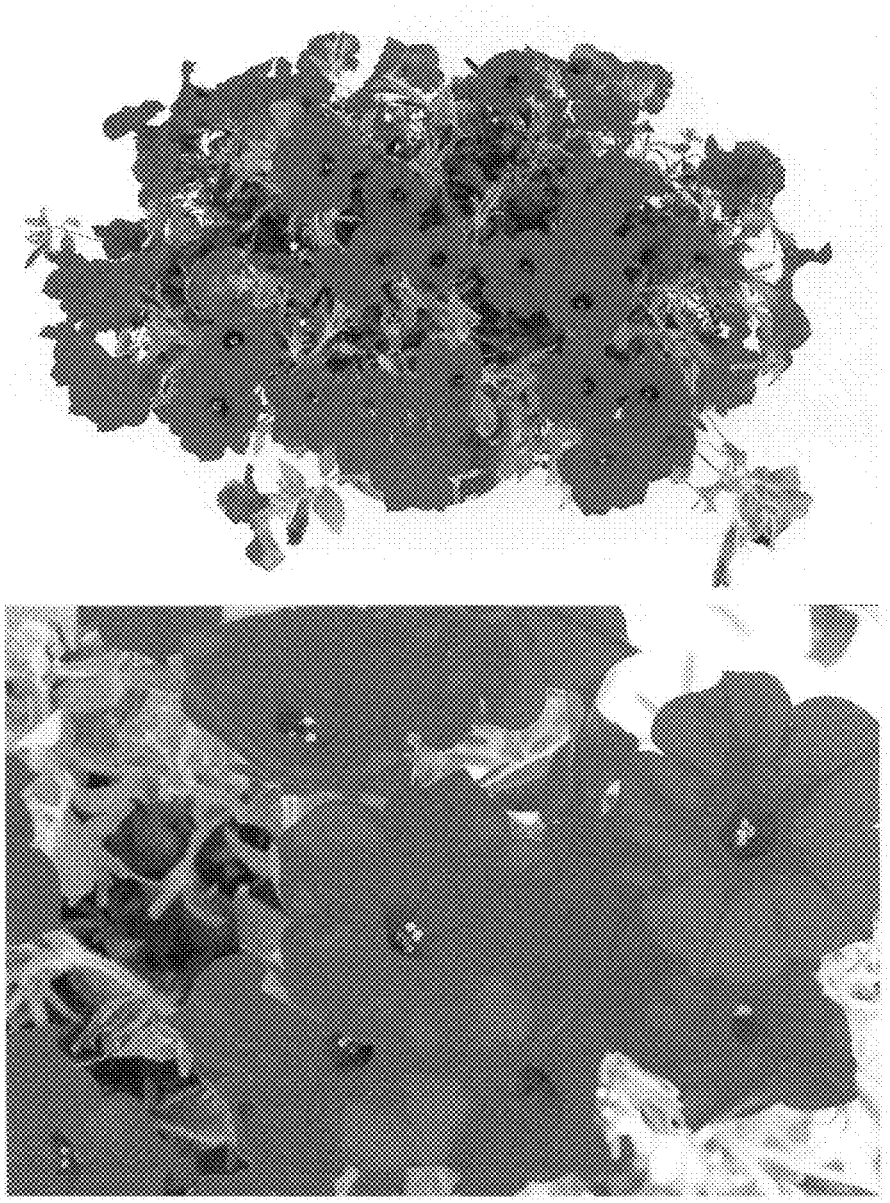

* * * * *